(12) United States Patent
Rack et al.

(10) Patent No.: US 6,548,677 B1
(45) Date of Patent: Apr. 15, 2003

(54) METHOD OF PRODUCING 2-ALKYL-3-(4,5-DIHYDROISOXAZOLE-3-YL)-HALOBENZENES

(75) Inventors: Michael Rack, Heidelberg; Norbert Götz, Worms; Helmut Hagen, Frankenthal; Wolfgang von Deyn, Neustadt; Ernst Baumann, Dudenhofen; Rene Lochtman, Mannheim; Joachim Gebhardt, Wachenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/856,037

(22) PCT Filed: Nov. 17, 1999

(86) PCT No.: PCT/EP99/08844

§ 371 (c)(1), (2), (4) Date: May 17, 2001

(87) PCT Pub. No.: WO00/29395

PCT Pub. Date: May 25, 2000

(65) Prior Publication Data (65)

(30) Foreign Application Priority Data

Nov. 18, 1998 (DE) ......... 198 53 039

(51) Int. Cl.⁷ ......... C07D 261/18
(52) U.S. Cl. ......... 548/240
(58) Field of Search ......... 548/240, 241

(56) References Cited

U.S. PATENT DOCUMENTS

| 6,004,903 A | 12/1999 | von Deyn | |
| 6,124,469 A | * 9/2000 | Rheinheimer et al. | 548/240 |

FOREIGN PATENT DOCUMENTS

| WO | 96/26200 | 8/1996 |
| WO | 98/31676 | 7/1998 |
| WO | 99/58509 | 11/1999 |

* cited by examiner

Primary Examiner—Floyd D. Higel
Assistant Examiner—Kamal Saeed
(74) Attorney, Agent, or Firm—Keil & Weinkauf

(57) ABSTRACT

A novel process for preparing the compounds of the formula I

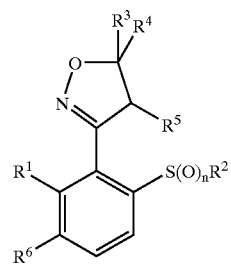

where:
n is 0, 1 or 2;
$R^1$, $R^2$ are $C_1$–$C_6$-alkyl;
$R_3$, $R_4$, $R_5$ are hydrogen or $C_1$–$C_6$-alkyl, or $R^4$ and $R^5$ together form a bond;
$R^6$ is Cl, Br,
which comprises a synthesis sequence starting from 1,2-dialkylbenzenes of the formula II

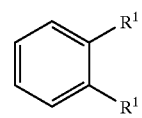

with subsequent halogenation to give 3,6-dihalo-1,2-dialkylbenzenes, haloalkylation to give benzyl bromides, oxidation to give benzaldehydes, oximation, reaction with alkenes to give isoxazoles, conversion into thioethers and, if appropriate, oxidation to give sulfenyl or sulfonyl derivatives of the formula I.

14 Claims, No Drawings

METHOD OF PRODUCING 2-ALKYL-3-(4,5-DIHYDROISOXAZOLE-3-YL)-HALOBENZENES

This application is a 371 of PCT/EP08844 filed on Nov. 17, 1999.

The present invention provides a process for preparing 2-alkyl-3-(4,5-dihydroisoxazol-3-yl)halobenzenes.

2-Alkyl-3-(4,5-dihydroisoxazol-3-yl)halobenzenes are starting materials for preparing 2-alkyl-3-(4,5-dihydroisoxazol-3-yl)acylbenzenes which can be used in the field of crop protection. Such compounds are described as herbicidally active compounds in WO 98/31681, for example.

It is an object of the present invention to provide an improved preparation process for 3-heterocyclyl-substituted benzoyl derivatives as described, for example, in WO 98/31681. The preparation process described in WO 98/31681 for the 2-alkyl-3-(4,5-dihydroisoxazol-3-yl)acylbenzenes and their precursors (2-alkyl-3-(4,5-dihydroisoxazol-3-yl)bromobenzenes) is not ideal for the large-scale industrial preparation of these compounds, since the synthesis involves a plurality of steps and the yield of the respective end product is relatively low, based on the starting materials employed in the first step of the synthesis.

We have found that this object is achieved by the process according to the invention, which permits the preparation of the 3-heterocyclyl-substituted benzoyl derivatives or their various precursors in good yield and on an advantageous economical scale. The process according to the invention has the advantage that the total yield of the end products in question, based on the starting materials used, is higher than the yield in the processes described in WO 98/31681. Furthermore, the starting materials can be prepared in a simple manner or can be purchased even in relatively large amounts, by a number of independent suppliers of raw materials, so that overall, a cheaper, economical and safe process for the large-scale industrial preparation of herbicidally active compounds is provided.

The present invention provides a process for preparing the compounds of the formula I

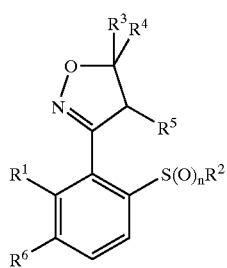

I where:
n is 0,1 or 2;
$R^1$, $R^2$ are $C_1$–$C_6$-alkyl;
$R^3$, $R^4$, $R^5$ are hydrogen or $C_1$–$C_6$-alkyl, in particular methyl, or $R^4$ and $R^5$ together form a bond;
$R^6$ is Cl, Br, which comprises one or more of the following process steps a)–g):

a) halogenation of a 1,2-dialkylbenzene of the formula II

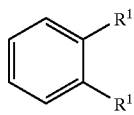

II in which the radicals $R^1$ can be identical or different and are as defined above with halogens, in particular chlorine or bromine, to give the 3,6-dihalo-1,2-dialkylbenzenes of the formula III

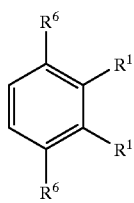

III b) reaction of a 3,6-dihalo-1,2-dialkylbenzene of the formula III with hydrogen peroxide and a halogenating agent, preferably HBr, to give the benzyl halides, in particular the benzyl bromides, of the formula IV

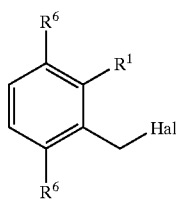

IV in which the radicals $R^1$ and $R^6$ are as defined above;

c) oxidation of the benzyl bromides of the formula IV with an oxidizing agent to give the aldehydes of the formula V

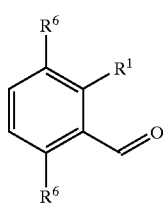

V in which the substituents $R^1$ and $R^6$ are as defined above;

d) reaction of the compounds of the formula V with hydroxylamine and base to give the corresponding oximes of the formula VI

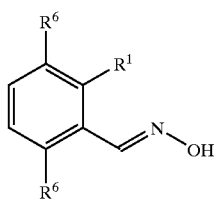

VI in which the substituents $R^1$ and $R^6$ are as defined above;

e) reaction of the oximes of the formula VI with an alkene of the formula VII

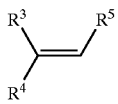

VII in which $R^3$ to $R^5$ are as defined in claim 1, in the presence of a hypochlorite, to give the 4,5-dihydroisoxazole of the formula VIII

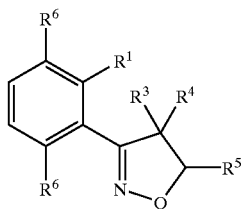

VIII in which $R^1$ and $R^3$ to $R^6$ are as defined in claim 1;

f) reaction of the compound of the formula VIII with metal thiolates of the formula IX

IX in the presence of a solvent to give the thioethers of the formula X

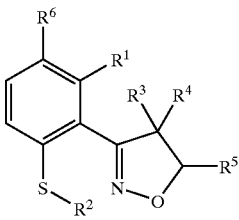

X in which $R^1$ to $R^6$ are as defined in claim 1;

g) if appropriate reaction of the thioethers of the formula X with an oxidizing agent to give the corresponding alkylsulfonyl or alkylsulfenyl derivatives of the formula I where n is the number 1 or 2.

In all cases, $C_1$–$C_6$-alkyl is a straight-chain or branched alkyl group having 1–6 carbons, such as, for example, methyl, ethyl, n-propyl, isopropyl, n-butyl, isobutyl, n-pentyl or n-hexyl. This applies analogously to the $C_1$–$C_6$-alkoxy group.

$R^4$ and $R^5$ together may also represent a bond, resulting in the corresponding isoxazole derivatives. In this case, $R^3$ is preferably hydrogen.

The reaction sequence leading to the compounds of the formula I is compiled in the synoptical scheme below:

Scheme 1:

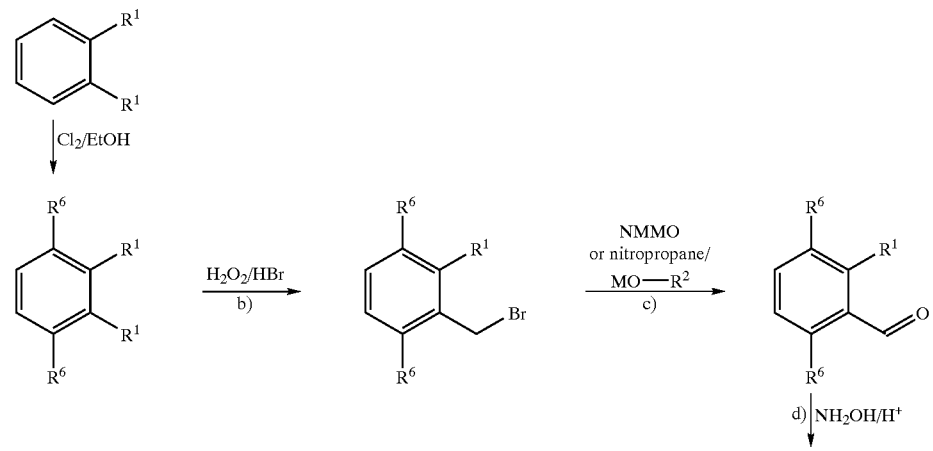

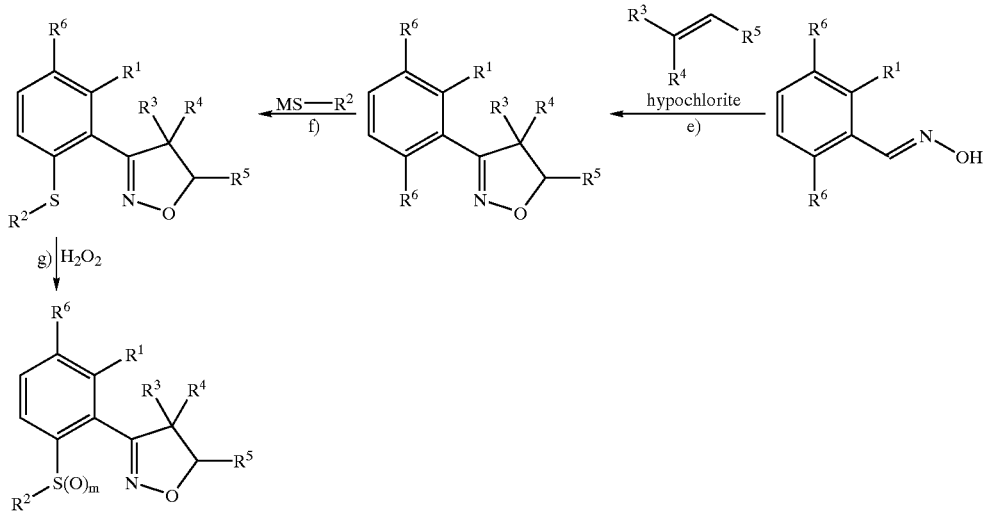

Hereinbelow, the individual steps are briefly illustrated in more detail.

1. Step a)

The halogenation is carried out by methods known from the literature, preferably using chlorine gas. Suitable solvents are alcohols, such as, for example, ethanol.

2. Step b)

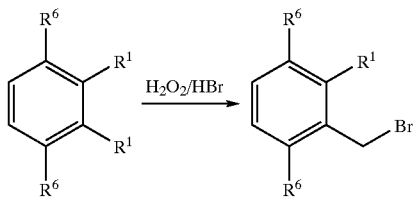

The reaction is carried out under the following conditions: solvent: solvents which are inert to the bromination, such as: benzene, tert-butylbenzene, tert-amylbenzene, halogenated hydrocarbons, such as methylene chloride, chloroform, chlorobenzene 1,2-dichloroethane, carbon tetrachloride, dichlorobenzene or trichlorobenzene. Mixtures of these solvents may also be used. Brominating agent: bromine, bromine salts or HBr, preferably in an aqueous solution. Particular preference is given to using technical-grade azeotropic mixtures of HBr.

3. Step c)

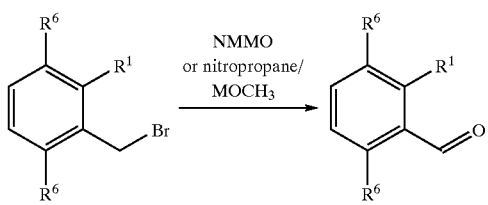

NMMO: N-methylmorpholine N-oxide

Suitable for the oxidation are, for example, oxidizing agents, such as peracids, peroxides, hypochlorite, chlorine, sodium bromate and potassium peroxodisulfate; hydrogen peroxide is particularly suitable. It is known from the literature (DE-29 48 058) that alkyl halides and benzyl halides can be oxidized to the corresponding carbonyl compounds using amine oxides of tertiary amines or pyridine. The reaction is carried out under the following conditions: amine oxides: amine oxides having aliphatic, cycloaliphatic and aromatic radicals, such as trimethylamine, dimethylcyclopentylamine, dimethylamine. Furthermore amine oxides having cycloaliphatic radicals which are interrupted by heteroatoms (O; N). N-alkyl- and N-aryl-substituted piperidines, piperazines and morpholines.

Alternatively, it is possible to apply the method described in U.S. Pat. No. 2,902,515, where allyl halides are reacted with alkali metal nitronates to give the corresponding aldehydes. The conditions are, for example, the following: solvent: alcohols, such as methanol, ethanol, isopropanol, ethers, such as dioxane, THF, dipolar aprotic solvents, such as, for example, N,N-dialkylformamides, -acetamides, N-methylpyrrolidone, dimethylpropylene urea; tetramethyl urea, DMF, NMP, acetonitrile. Preference is given to methanol. The nitronates are generated as follows: reaction of lower nitroalkanes with alkali metal hydroxides (aqueous NaOH or KOH) or reaction of lower nitroalkanes with alkali metal alkoxides, such as KOtBu in butanol or sodium methoxide in methanol. The resulting nitronates are reacted with the benzyl halides. The reaction is carried out at temperatures from −10° C. to 80° C., preferably from 0° C. to 50° C. This is followed by aqueous work-up.

4. Step d)

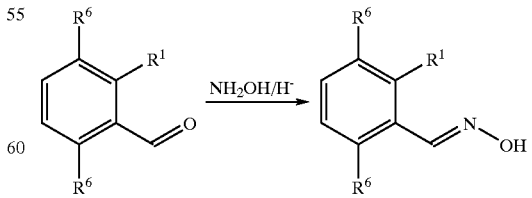

The benzaldoxime can be obtained in virtually quantitative yield by standard processes starting from the corresponding aldehydes, by reaction with hydroxylamine in the presence of acid.

5. Step e)

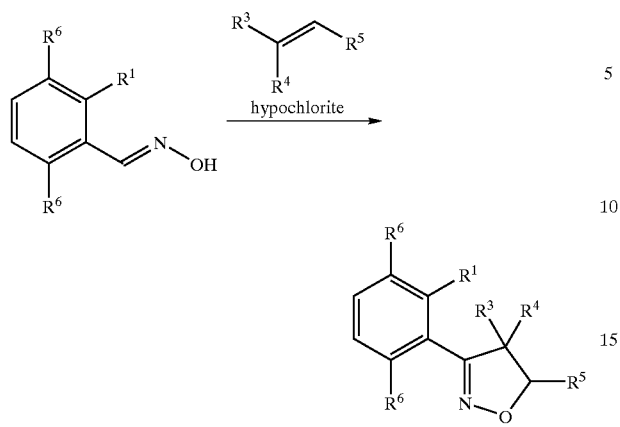

6. Step f)

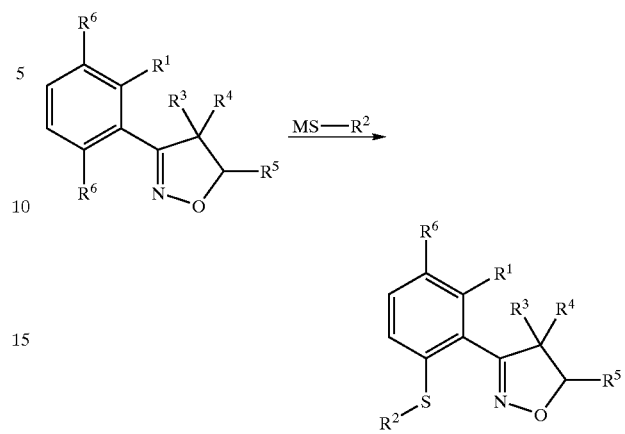

The reaction of the benzaldoxime of the formula VI with alkenes of the formula VII to give compounds of the formula VIII proceeds via different intermediates. Since the first reaction step comprises the formation of an intermediate hydroxamic acid halide, a suitable oxidizing agent and a source of halogen or even the halogen itself have to be present. The second reaction step is the elimination of hydrogen halide giving the nitrile oxide, which reaction requires basic conditions. The final, third step is the cycloaddition of the nitrile oxide to the alkene.

This sequence can be carried out stepwise by customary processes using, for example, the free halogens bromine or chlorine for forming the hydroxamic acid halide. Since the hydroxamic acid halides have a tendency to decompose, they have to be converted quickly, using a base, into the even more sensitive nitrile oxides, which in most cases are trapped in situ with the alkene.

In the process according to the invention, these individual steps have now been combined advantageously in a "one-pot reaction". To this end, the reaction is generally carried out in a solvent such as, for example, a halogenated alkane, such as dichloroethane or methylene chloride, or an aromatic, such as benzene, toluene, chlorobenzene, nitrobenzene or xylene, which dissolves the organic component but does not interfere with the reaction. An aqueous alkali metal hypohalite solution, preferably 1–2 equivalents of commercially available sodium hypochlorite solution, is added as halogenating agent and simultaneously as base, and the alkene is added in parallel or immediately afterwards. Thus, the reaction mixture is usually biphasic, since the organic solvent and the alkali metal hypohalite solution mix only incompletely. To complete the conversion, it may be advantageous to add 3–50% of sodium acetate or potassium acetate; however, this is not essential.

Gaseous alkenes of the formula VII are introduced, liquid alkenes are metered in correspondingly. The alkenes are generally employed in a molar ratio of from 1 to 5:1, based on the oxime VI.

The reaction is carried out at 0–80° C., preferably 20–50° C. The reaction is carried out under a pressure of 0–20 bar, preferably 0–6 bar.

The reaction of alkali metal thioalkylates or copper thioalkylates with aromatic halogen compounds affords aromatic alkyl thioethers.

The reaction is carried out under the following conditions: solvent: alcohols, such as methanol, ethanol, propanol, tert-butanol, water, ethers, such as dioxane, THF, polar aprotic solvents, for example N,N-dialkylformamides, -acetamides, N-methylpyrrolidone, dimethylpropyleneurea; tetramethylurea, acetonitrile, propionitrile, dimethyl sulfoxide; preferably: methanol, DMF, NMP. Temperature: 0° C. to 170° C., preferably 30° C. to 120° C., particularly preferably 40° C. to 100° C.

Practice: The alkali metal thioalkylate, for example sodium thiomethylate, can be employed as a solid or as an aqueous or methanolic solution or be prepared and employed in situ from the alkyl mercaptan, for example methyl mercaptan, and an alkali metal alkoxide or hydroxide or alkaline earth metal alkoxide or hydroxide base, for example sodium methoxide, potassium ethoxide, sodium hydroxide or potassium hydroxide. The reaction can also be carried out under reduced pressure, by additionally adding a high-boiling dipolar aprotic solvent, with distillative removal of the low-boiling solvent, for example water or methanol. By adding copper powder (0.01–10 mol %) as catalyst, it is frequently possible to achieve a complete and faster reaction. The thioalkylation is generally carried out at 0–100° C., preferably at 20–80° C.

7. Step g)

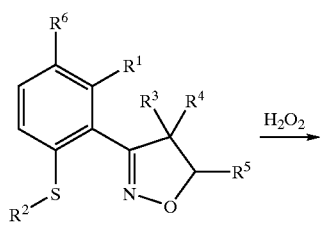

-continued

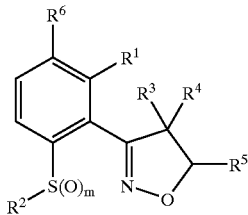

The oxidation is carried out similarly to the reaction of the chlorine derivative ($R^1$=Cl), described in: WO 98/31681 (cf. p. 8 line 32 to p. 11, line 25).

The invention is illustrated in more detail in the embodiments below.

EXAMPLE 1

Preparation of 3,6-dichloro-1,2-xylene

The chlorination of 1,2-xylene is carried out by methods known from the literature, using chlorine gas. The solvent used for xylene is ethanol.

EXAMPLE 2

Preparation of 3,6-dichloro-2-methylbenzyl bromide 170.1 g (0.97 mol) of 3,6-dichloro-1,2-xylene are initially charged in 1180 ml of chlorobenzene, and 4.9 g of conc. $H_2SO_4$ and 203.1 g (1.18 mol) of 47% strength hydrobromic acid are added. The mixture is heated to 70° C., and 0.9 g of AIBN are added. Over a period of 5 h, 353.7 g (1.04 mol) of a 10% strength solution of hydrogen peroxide are added at 70–75° C., the mixture is stirred at 70–75° C. for 30 min, washed twice with 400 ml of water and once with 400 ml of saturated sodium bicarbonate solution, and the chlorobenzene is then distilled off.

This gives 242.9 g of a product which is 78.4% pure (9.5% of starting material, 10.4% of dibromo compound). Yield: 77.2%. GC/MS: m/z: 252.

EXAMPLE 3

Preparation of 3,6-dibromo-2-methylbenzyl bromide 183.2 g (0.65 mol) of 3,6-dibromo-1,2-xylene are initially charged in 750 ml of chlorobenzene, and 2 g of conc. $H_2SO_4$ and 270.7 g (1.57 mol) of 47% strength hydrobromic acid are then added. The reaction mixture is heated to 70° C. and 0.3 g of AIBN are added. Over 14 h, 237.7 g (0.7 mol) of a 10% strength solution of hydrogen peroxide are added at 75–77° C., the mixture is stirred for another 120 min., washed 2× with 250 ml of water and once with 250 ml of saturated sodium bicarbonate solution, and the chlorobenzene is then distilled off.

This gives 219.3 g of a product which is 72.3% pure (15.3% of starting material, 6.4% of dibromo compound). Yield: 70.9%. GC/MS: m/z: 340.

EXAMPLE 4

Preparation of 3,6-dichloro-2-methylbenzaldehyde 122.4 g (0.68 mol) of a 30% strength solution of sodium methoxide are dissolved in 1030 ml of methanol, and 56.4 g ( 0.57 mol) of 90% pure 2-nitropropane and 188.5 g (0.52 mol) of 61.6% pure 3,6-dichloro-2-methylbenzyl bromide are then added. The reaction is exothermic to 53° C., and the mixture is then stirred for 90 min. The reaction mixture is poured into 2.5 l of water, the pH is adjusted to pH 7.0 using 10% strength HCl, the mixture is extracted three times with 1 l of ethyl acetate, and the organic phases are combined, washed twice with 500 ml of saturated NaCl solution, dried over $Na_2SO_4$ and concentrated under reduced pressure: the 161.0 g of crude product are distilled using a 10 cm column packed with 10 mm Raschig rings. The crystals from the last fractions are filtered. This gives 9.8 g comprising 85.9% of the desired product and 4.5% and 6.9% of isomers. Yield: 9.7%. The residue is distilled over a Spaltrohr column, giving another 3.2 g of 94.3% pure product.

EXAMPLE 5

Preparation of 3,6-dichloro-2-methylbenzaldehyde 67.4 g (0.19 mol) of 72.2% pure 3,6-dichloro-2-methylbenzyl bromide is initially charged in 280 ml of acetonitrile. At 0–5° C., a solution of 54.0 g (0.46 mol) of N-methylmorpholine N-oxide and 280 ml of acetonitrile is added over a period of 25 min, and the mixture is stirred at 0–8° C. for 1 h. The precipitate is filtered off with suction and taken up in 280 ml of acetonitrile, and 250 g (0.42 mol) of 20% strength NMO in acetonitrile are then added at 40° C. The reaction mixture is stirred at 40° C. for 1 h and concentrated under reduced pressure, the residue is taken up in 250 ml of methylene chloride and the mixture is washed three times with 250 ml of water, dried over $Na_2SO_4$ and concentrated under reduced pressure. This gives 32.9 g of a product which is 92.6% pure.

Yield: 84.2%. $^1$H-NMR (CDCl$_3$): 2.6 ppm (s, 3H, Me), 7.2 ppm (d, 1H, arom-H), 7.45 ppm (d, 1H, arom-H), 10.5 ppm (s, 1H, CHO).

EXAMPLE 6

Preparation of 3,6-dichloro-2-methylbenzaldoxime 198 g (0.975 mol) of 93% pure 3,6-dichloro-2-methylbenzaldehyde and 416.2 g (0.634 mol) of a 25% strength aqueous solution of hydroxylamine sulfate are mixed in 1.5 l of toluene and heated at 80° C. Over a period of 2 h, 109.2 g (1.36 mol) of 50% strength NaOH are then added dropwise such that the pH is between 3 and 5. Stirring at 80° C. is continued for 1 h, and the phases are then separated at 80° C. The organic phase is washed once with 250 ml of water. The organic phase is concentrated and the residue is recrystallized from cyclohexane. This gives 165.4 g of the aldoxime (83.3% of theory). $^1$H-NMR: (DMSO-D$_6$): 2.4 ppm (s, 3H, Me), 7.4 ppm (d, 1H, arom-H), 7.5 ppm (d, 1H, arom-H), 8.3 ppm (s, 1H, NH), 11.7 ppm (s, 1H, OH).

EXAMPLE 7

Preparation of 3,6-dibromo-2-methylbenzaldoxime 10 g (0.42 mol) of 3,6-dibromo-2-methylbenzaldehyde and 178.5 g (0.272 mol) of a 25% strength aqueous solution of hydroxylamine sulfate are mixed in 1.2 l of toluene and heated at 80° C. Over a period of 2 h, 109.2 g (1.36 mol) of 50% strength NaOH are then added dropwise such that the pH is between 3 and 5. Stirring at 80° C. is continued for 1 h, the mixture is stirred at room temperature overnight and the phases are then separated at 80° C. The organic phase is washed once with 350 ml of water. The organic phase is concentrated and the residue is recrystallized from cyclohexane. This gives 113.9 g (93% of theory) of the aldoxime.

1H-NMR: (DMSO-$D_6$): 2.45 ppm (s, 3H, Me), 7.5 ppm (d, 1H, arom-H), 7.6 ppm (d, 1H, arom-H), 8.1 ppm (s, 1H, NH), 11.65 ppm (s, 1H, OH).

EXAMPLE 8

Preparation of 3-(3,6-dichloro-2-methylphenyl)-4,5-dihydroisoxazole

In a pressure container, 50 g (0.25 mol) of 3,6-dichloro-2-methylbenzaldoxime are dissolved in 750 ml of methylene chloride. 16 g of ethylene are applied, and 620 g of a 12.5% strength solution of NaOCl are then pumped in at room temperature, and the mixture is stirred overnight. The pressure vessel is vented, and the organic phase is then separated off, washed once with water and dried, and the solvent is removed under reduced pressure. This gives 58 g of product (95% pure) (95% of theory). $^1$H-NMR (DMSO-$D_6$): 2.3 ppm (s, 3H, Me), 3.3 ppm (t, 2H, CH2), 4.5 ppm (t, 2H, CH2), 7.45 ppm (d, 1H, arom-H), 7.6 ppm (d, 1H, arom-H).

EXAMPLE 9

Preparation of 3-(3,6-dibromo-2-methylphenyl)-4,5-dihydroisoxazole 68 g (0.23 mol) of 3,6-dibromo-2-methylbenzaldoxime are dissolved in 750 ml of methylene chloride in a pressure container. 20 g of ethylene are applied, and 620 g of a 12.5% strength solution of NaOCl are then pumped in at room temperature, and the mixture is stirred overnight. The pressure vessel is vented, and the organic phase is then separated off, washed once with 250 ml of water and dried, and the solvent is removed under reduced pressure. This gives 77 g of product (95% pure) (99% of theory).

EXAMPLE 10

Preparation of 3-(3-chloro-2-methyl-6-methylthiophenyl)-4,5-dihydroisoxazole 20 g (0.083 mol) of 3-(3,6-dichloro-2-methylphenyl)-4,5-dihydroisoxazole are dissolved in 120 ml of NMP. At 0° C., 6.7 g (0.09 mol) of sodium thiomethoxide are added over a period of 40 min, and the mixture is then stirred overnight. The reaction mixture is stirred into 360 ml of water and extracted four times with 70 ml of toluene, the combined organic phases are washed once with 70 ml of water and the organic phase is concentrated. The residue (an isomer mixture) is distilled at 150–170° C. under a reduced pressure of 1 mbar. The main fraction is purified chromatographically. This gives 4.5 g of a product which is 83% pure (17% of theory).

EXAMPLE 11

Preparation of 3-(3-bromo-2-methyl-6-methylthiophenyl)-4,5-dihydroisoxazole 25 g (0.075 mol) of 3-(3,6-dibromo-2-methylphenyl)-4,5-dihydroisoxazole are initially charged in 12 mol of NMP. At a temperature of 100° C. and at a reduced pressure of 100 mbar, 29.3 g (0.09 mol) of a 21.5% strength methanolic solution of sodium thiomethoxide are added dropwise over a period of 40 min. The reaction mixture is stirred at 100° C. for 3 h and then stirred into 250 ml of water and extracted three times with 100 ml of toluene. The combined organic phases are washed once with 100 ml of water and then concentrated under reduced pressure. This gives 17.5 g of a dark oil. GC/MS shows, in addition to other isomers, 52.3% of the desired product. MSm/z: 287.

EXAMPLE 12

Preparation of 3-(3-chloro-2-methyl-6-methylsulfonylphenyl)-4,5-dihydroisoxazole 1.4 g (6.2 mmol) of 3-(3-chloro-2-methyl-6-methylthiophenyl)-4,5-dihydroisoxazole are dissolved in 3 ml of glacial acetic acid, and 30.7 mg of sodium tungstate dihydrate are added. At 25–40° C., 2.1 g (18.6 mmol) of hydrogen peroxide are added dropwise, and the reaction mixture is stirred for 3 h. The reaction mixture is then poured into 1.5 ml of water, the mixture is cooled to 0° C. and the resulting precipitate is filtered off with suction, washed five times with 10 ml of water and dried under reduced pressure. This gives 1.23 g of product.

What is claimed is:

1. A process for preparing an isoxazole of formula I

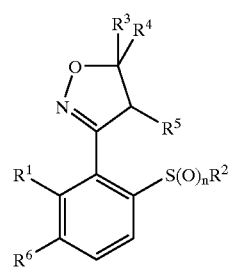

I where:

n is 0,1 or 2;

$R^1$, $R^2$ are $C_1$–$C_6$-alkyl;

$R^3$, $R^4$, $R^5$ are hydrogen or $C_1$–$C_6$-alkyl, or $R^4$ and $R^5$ together form a bond;

$R^6$ is Cl, Br, which comprises one or more of the following process steps:

a) halogenating a 1,2-dialkylbenzene of formula II

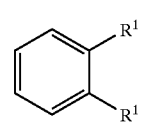

II in which the radicals $R^1$ can be identical or different and are as defined above with a halogen to give a 3,6-dihalo-1,2-dialkylbenzene of formula III

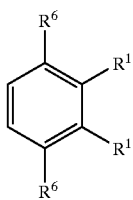

III b) reacting a 3,6-dihalo-1,2-dialkylbenzene of formula III with hydrogen peroxide and a halogenating agent to give a benzyl halide of formula IV

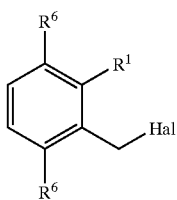

IV in which the radicals $R^1$ and $R^6$ are as defined above;

c) oxidizing a benzyl halide of formula IV with an oxidizing agent to give an aldehyde of formula V

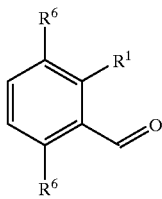

V in which the substituents $R^1$ and $R^6$ are as defined above;

d) reacting a compound of formula V with hydroxylamine and base to give the corresponding oxime of formula VI

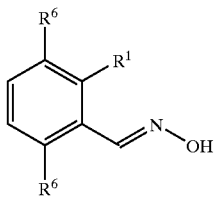

VI in which the substituents $R^1$ and $R^6$ are as defined above;

e) reacting an oxime of formula VI with an alkene of formula VII

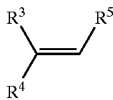

VII in which $R^3$ to $R^5$ are as defined above, in the presence of an alkali metal hypohalide, to give 4,5-dihydroisoxazole of formula VIII

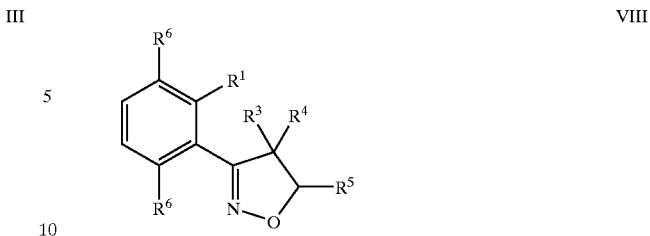

VIII in which $R^1$ and $R^3$ to $R^6$ are as defined above;

f) reacting a compound of formula VIII with a metal thiolate of formula IX

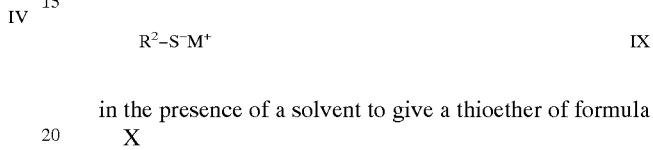

IX in the presence of a solvent to give a thioether of formula X

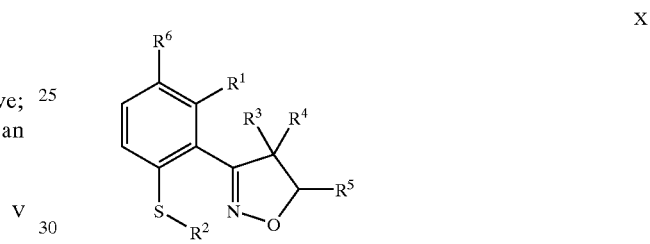

X in which $R^1$ to $R^6$ are as defined above;

g) reacting a thioether of formula X with an oxidizing agent to give the corresponding alkylsulfonyl or an alkylsulfenyl derivative of formula I where n is the number 1 or 2, and carrying out process steps a), b) and c) in succession in preparing a compound of formula V.

2. A process as claimed in claim 1 where $R^3$ is hydrogen or methyl.

3. A process as claimed in claim 1 where $R^4$ is hydrogen or methyl.

4. A process as claimed in claim 1 where $R^5$ is hydrogen or methyl.

5. A process as claimed in claim 1 where $R^3$, $R^4$ and $R^5$ are hydrogen.

6. A process as claimed in claim 1 where $R^6$ is bromine.

7. A process as claimed in claim 1 where $R^6$ is chlorine.

8. A process as claimed in claim 1 where one of the radicals $R^1$ in formula II is a methyl group.

9. A process as claimed in claim 1 for preparing a compound selected from the group consisting of:
3-(3-chloro-2-methyl-6-methylthiophenyl)-4,5-dihydroisoxazole;
3-(3-bromo-2-methyl-6-methylthiophenyl)-4,5-dihydroisoxazole;
3-(3-chloro-2-methyl-6-methylsulfonylphenyl)-4,5-dihydroisoxazole; and
3-(3-bromo-2-methyl-6-methylsulfonylphenyl)-4,5-dihydroisoxazole.

10. The process of claim 1, wherein the halogen is chlorine, the halogenating agent is HBr and the benzyl halide in step b) is benzyl bromide.

11. A process as claimed in claim 1, wherein the halogenating agent of step a) is chlorine.

12. A process as claimed in claim 1, wherein the halogenating agent of step b) is Hbr.

13. A process as claimed in claim 1 wherein the step e) is carried out in the presence of an alkali metal hypochlorite.

14. A process as claimed in claim 1 wherein the halogenating agent of step a) is chlorine; and wherein the halogenating agent of step b) is Hbr; and wherein step e) is carried out in the presence of an alkali metal hypochlorite.

* * * * *

UNITED STATES PATENT AND TRADEMARK OFFICE
CERTIFICATE OF CORRECTION

PATENT NO.    : 6,548,677 B1
DATED         : April 15, 2003
INVENTOR(S)   : Rack et al.

It is certified that error appears in the above-identified patent and that said Letters Patent is hereby corrected as shown below:

<u>Column 12,</u>
Line 55, delete "one or more of".

<u>Column 14,</u>
Line 34, after "g)" insert -- optionally --;
Line 37, after "1 or 2" delete the rest of the claim through the end of line 39.

Signed and Sealed this

Twenty-third Day of September, 2003

JAMES E. ROGAN
*Director of the United States Patent and Trademark Office*